US00PP10065P

Jnited States Patent [19]

Vain

[11] Patent Number: Plant 10,065

[45] Date of Patent: Oct. 14, 1997

4] CHRYSANTHEMUM PLANT NAMED 'DARK FIJI'

5] Inventor: Peter Wain, Hayling Island, United Kingdom

3] Assignee: Cleangro Ltd., Chichester, United Kingdom

1] Appl. No.: 648,928

2] Filed: May 16, 1996

1] Int. Cl.[6] ..... A01H 5/00

2] U.S. Cl. ..... Plt./76

[58] Field of Search ..... Plt./76, 80, 81

*Primary Examiner*—Howard J. Locker

*Attorney, Agent, or Firm*—C. A. Whealy

[57] ABSTRACT

A distinct cultivar of Chrysanthemum plant named Dark Fiji, characterized by its flat capitulum form; decorative-type inflorescences; early flowering; lavender pink ray florets; numerous inflorescences per plant when grown as a spray; numerous ray florets per inflorescence; and strong peduncles and stems.

1 Drawing Sheet

1

The present invention relates to a new and distinct cultivar ' Chrysanthemum plant, botanically known as *Dendranema grandiflora* and referred to by the cultivar name Dark ji.

The new cultivar is a spontaneous mutation of the comercial cultivar Fiji (U.S. Plant patent application Ser. No. 3/648,930). The new cultivar was discovered and selected May, 1992, by the inventor in a controlled environment in avant, Hampshire, United Kingdom, as a single plant nong a population of plants of the cultivar Fiji. This single ant consistently formed inflorescences having lavender nk ray florets compared to the lighter pink-colored ray orets of plants of the cultivar Fiji. Other new cultivars have so been discovered and selected by the inventor as sponneous mutations of the commercial cultivar Fiji. These clude, but are not limited to, 'White Fiji' (disclosed in U.S. ant patent application Ser. No. 08/649,955) with whitelored ray florets and 'Bright Yellow Fiji' (disclosed in U.S. ant patent Ser. application No. 08/648,927) with bright llow-colored ray florets.

Asexual reproduction of the new cultivar by terminal ittings taken at Havant, Hampshire, United Kingdom, has own that the unique features of this new Chrysanthemum e stable and reproduced true to type in successive generaons.

The following traits have been repeatedly observed and e determined to be the unique characteristics of Dark Fiji. ese characteristics in combination distinguish Dark Fiji as new and distinct cultivar:

1. Flat capitulum form.
2. Decorative-type inflorescences.
3. Can be produced as a spray or standard cut Chrysanemum.
4. Flowers after exposure to about eight weeks of short ys.
5. Lavender pink ray florets.
6. Numerous inflorescences per plant when grown as a ray.
7. Numerous ray florets per inflorescence.
8. Strong peduncles and stems.

The cultivar Dark Fiji has not been observed under all ssible environmental conditions. The phenotype may vary mewhat with variations in environment such as temperare, daylength and light intensity, without, however, any riance in genotype.

Plants of the new Chrysanthemum are similar to the ltivar Dolly (not patented). However, in side-by-side mparisons conducted in Oxnard, Calif., under commercial actice, plants of the new Chrysanthemum differed from ants of the cultivar Dolly in the following characteristics:

2

1. Plants of the new Chrysanthemum have smaller leaves than plants of the cultivar Dolly.
2. Plants of the new Chrysanthemum have larger inflorescences than plants of the cultivar Dolly.
3. Ray florets of plants of the new Chrysanthemum are darker pink than ray florets of plants of the cultivar Dolly.
4. Ray florets of plants of the new Chrysanthemum are cupped whereas ray florets of plants of the cultivar Dolly are flat.
5. The lower peduncles of plants of the new Chrysanthemum are shorter than the lower peduncles of plants of the cultivar Dolly.

The accompanying colored photograph illustrates the overall appearance of the new cultivar, showing the colors as true as it is reasonably possible to obtain in colored reproductions of this type.

The photograph comprises a side perspective view of a typical flowering stem of Dark Fiji grown as a spray (terminal inflorescence removed). The ray floret color in the photograph appears darker than the actual color due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with average night temperatures of 18C, average day temperatures of 24C, and light levels ranging from 2,000 (cloudy conditions) to 8,000 (sunny conditions) footcandles.

After sticking unrooted cuttings of the new cultivar in early January, plants received 14 long day/short nights followed by short day/long nights until flowering in mid-March. Immature terminal inflorescences were removed and flowering stems were grown as sprays. Measurements and numerical values represent ranges or averages for six typical flowering stems.

Botanical classification: *Dendranthema grandiflora* cultivar Dark Fiji.

Commercial classification: Decorative cut chrysanthemum.

Parentage: Spontaneous mutation of the cultivar Fiji (U.S. patent application Ser. No. 08/648,930).

Propagation:

*Type.*—Terminal tip cuttings.

*Time to rooting.*—7 to 10 days with soil temperatures of 22C.

*Rooting habit.*—Fine, fibrous and well-branched.

Plant Description:

*Appearance.*—Perennial herbaceous decorative-type cut flower. Stems upright, uniform habit and freely branching. Can be grown as a spray (center bud removed) or as a standard (lateral buds removed). Flowering stem length is about 82 cm.

*Vigor.*—Moderate.

*Foliage description.*—Leaf arrangement: Alternate. Leaf size, fully expanded: Length: 10 to 11 cm. Width: 5.5 to 6 cm. Leaf apex: Acuminate. Leaf base: Attenuate. Leaf margin: Palmately lobed. Leaf texture: Upper and under surfaces slightly pubescent. Veins prominent on under surface. Petiole length: 2 to 2.5 cm. Color: Young foliage upper surface: 147A. Young foliage under surface: 147B. Mature foliage upper surface: 147A. Mature foliage under surface: 147B. Venation upper surface: 147B. Venation under surface: 147B. Petiole: 147A.

Flowering description:

*Appearance.*—Decorative inflorescence form. Inflorescences borne on terminals above foliage. Florets arranged acropetally on a flat capitulum. Can be grown as a spray or as a standard.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to about 2 weeks of long day/short night conditions after planting followed by photoinductive short day/long night conditions, flower about 54 days later.

*Quantity of inflorescences.*—10 to 12 inflorescences per flowering stem.

*Bud.*—Size, showing color: Length: About 9 mm. Width: About 8 mm. Color: 75A.

*Inflorescence size.*—Diameter: 7.5 to 8.5 cm. Depth (height): 1.3 to 1.5 cm.

*Ray florets.*—Shape: Elongated. Size: Length: 3.8 to 4.2 cm. Width: 1.2 to 1.5 cm. Apex: Rounded. Base: Acute. Margin: Entire. Texture: Satiny, smooth, glabrous, ribbed lengthwise. Aspect: Cupped. Number of ray florets per inflorescence: About 232. Color: When opening, upper surface: 75A. When opening, under surface: 75A. Mature, upper surface: 75A, color fades to 75B with further development. Mature, under surface: 75D, color does not fade with further development.

*Disc florets.*—Shape: Tubular. Size: Length: About 2 mm. Width: About 1 mm. Number of disc florets per inflorescence: About 8. Color: Immature: 154A. Mature: 12A.

*Peduncle.*—Aspect: Strong. Length: First peduncle: 7 to 8 cm. Fourth peduncle: 8 to 9.5 cm. Texture: Glabrous. Color: 137B.

*Reproductive organs.*—Androecium: Present on disc florets only. Anther color: 12A. Pollen: Moderate, 12A in color. Gynoecium: Present on both ray and disc florets. Style color: 154A.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named Dark Fiji, as illustrated and described.

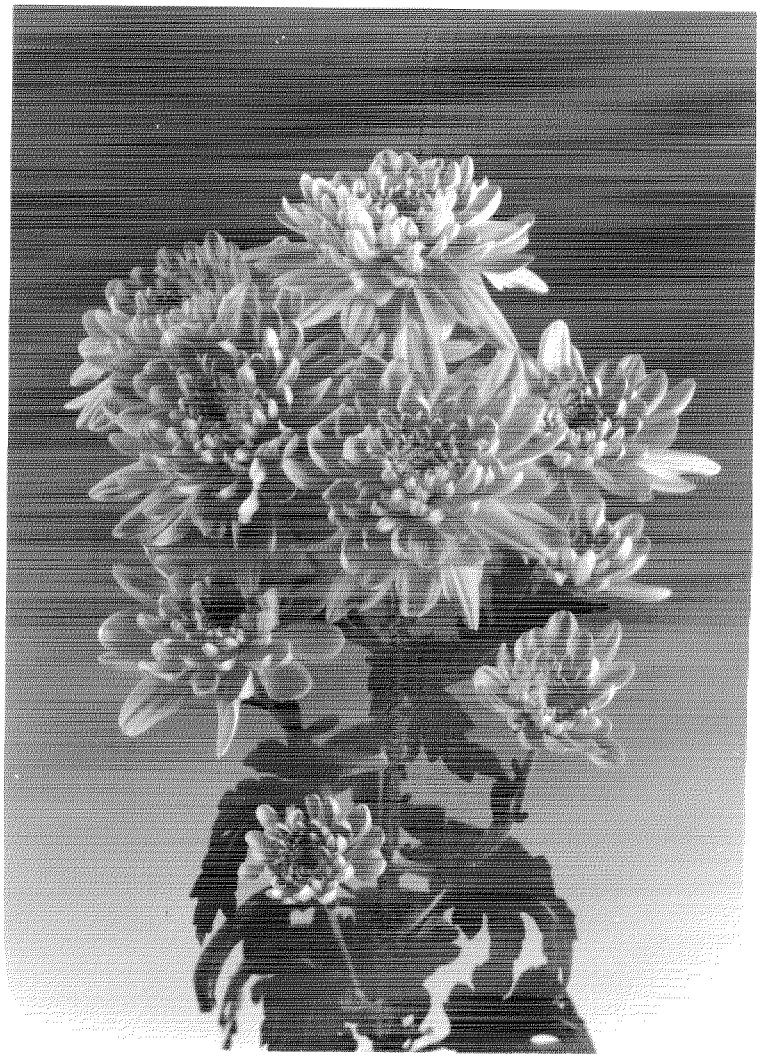

* * * * *